(12) United States Patent
Lauf et al.

(10) Patent No.: US 11,083,584 B2
(45) Date of Patent: Aug. 10, 2021

(54) EXPANDABLE WEDGE IMPLANT FOR OSTEOTOMIES OF THE EXTREMITIES

(71) Applicant: Life Spine, Inc., Huntley, IL (US)

(72) Inventors: Garrett D. Lauf, Hampshire, IL (US); Daniel P. Predick, West Lafayette, IN (US)

(73) Assignee: Life Spine, Inc., Huntley, IL (US)

( * ) Notice: Subject to any disclaimer, the term of this patent is extended or adjusted under 35 U.S.C. 154(b) by 232 days.

(21) Appl. No.: 16/371,090

(22) Filed: Mar. 31, 2019

(65) Prior Publication Data

US 2019/0298524 A1 Oct. 3, 2019

Related U.S. Application Data

(60) Provisional application No. 62/651,124, filed on Mar. 31, 2018.

(51) Int. Cl.
| | |
|---|---|
| *A61F 2/28* | (2006.01) |
| *A61F 2/44* | (2006.01) |
| *A61F 2/30* | (2006.01) |
| *A61B 17/80* | (2006.01) |

(52) U.S. Cl.
CPC ............ *A61F 2/28* (2013.01); *A61B 17/8095* (2013.01); *A61F 2/30749* (2013.01); *A61F 2/447* (2013.01); *A61F 2/4455* (2013.01); *A61F 2002/3037* (2013.01); *A61F 2002/3054* (2013.01); *A61F 2002/30242* (2013.01); *A61F 2002/30266* (2013.01); *A61F 2002/30405* (2013.01); *A61F 2002/30471* (2013.01); *A61F 2002/30507* (2013.01); *A61F 2002/30538* (2013.01); *A61F 2002/30579* (2013.01); *A61F 2002/30593* (2013.01); *A61F 2002/30785* (2013.01); *A61F 2002/30787* (2013.01); *A61F 2002/30904* (2013.01)

(58) Field of Classification Search
CPC ............................. A61F 2/28; A61B 17/8095
See application file for complete search history.

(56) References Cited

U.S. PATENT DOCUMENTS

| 5,554,191 A | * | 9/1996 | Lahille | ............... A61B 17/1757 |
| | | | | 623/17.11 |
| 6,102,950 A | * | 8/2000 | Vaccaro | ................... A61F 2/447 |
| | | | | 623/17.16 |
| 7,837,734 B2 | * | 11/2010 | Zucherman | ........... A61F 2/4425 |
| | | | | 623/17.15 |

(Continued)

*Primary Examiner* — Bruce E Snow
*Assistant Examiner* — Melissa A Hoban
(74) *Attorney, Agent, or Firm* — Foley & Lardner LLP (57) ABSTRACT

An expandable wedge implant for wedge osteotomies of the extremities has first and second components which are pivotally attached to each other such that up and down pivoting of the two components relative to one another causes increase and decrease of implant height. A pivot control structure is operably coupled to and between the two components to effect pivoting. Linear movement of a threaded ball on a threaded shaft associated with the first component while the threaded ball is concurrently constrained within an angled channel of the second component causes pivoting of the second component relative to the first component. Anchoring members associated with the first and second components attach the implant to adjacent vertebral bodies.

7 Claims, 7 Drawing Sheets

(56) References Cited

U.S. PATENT DOCUMENTS

| | | | |
|---|---|---|---|
| 2006/0022180 A1* | 2/2006 | Selness | A47B 91/028 |
| | | | 254/104 |
| 2008/0015603 A1* | 1/2008 | Collazo | A61B 17/157 |
| | | | 606/87 |
| 2008/0262500 A1* | 10/2008 | Collazo | A61B 17/8095 |
| | | | 606/88 |
| 2012/0215316 A1* | 8/2012 | Mohr | A61F 2/442 |
| | | | 623/17.16 |
| 2014/0172116 A1* | 6/2014 | Maxson | A61F 2/2846 |
| | | | 623/23.53 |
| 2014/0288653 A1 | 9/2014 | Chen | |
| 2016/0287403 A1* | 10/2016 | Suddaby | A61F 2/4425 |
| 2017/0000618 A1* | 1/2017 | Tyber | A61B 17/7291 |
| 2017/0216045 A1* | 8/2017 | Dewey | A61F 2/4611 |
| 2017/0296352 A1 | 10/2017 | Richerme et al. | |
| 2017/0367842 A1 | 12/2017 | Predick et al. | |
| 2018/0000609 A1* | 1/2018 | Hessler | A61F 2/4455 |

* cited by examiner

FIG. 14

EXPANDABLE WEDGE IMPLANT FOR OSTEOTOMIES OF THE EXTREMITIES

CROSS-REFERENCE TO RELATED APPLICATIONS

This U.S. non-provisional patent application claims the benefit of and/or priority under 35 U.S.C. § 119(e) to U.S. provisional patent application Ser. No. 62/651,124 filed Mar. 31, 2018 titled "Expandable Wedge Implant for Osteotomies of the Extremities" the entire contents of which is specifically incorporated herein by reference.

FIELD OF THE INVENTION

The present invention relates to orthopedic implants for the extremities and, more particularly, to expandable orthopedic implants for osteotomies of the extremities.

BACKGROUND OF THE INVENTION

An osteotomy is a surgical procedure that cuts a bone and/or resects a piece or pieces of bone. The surgical procedure is most often used to treat disease of or trauma to bone, a bone joint, and/or to correct a bone or bone joint deformity. In many circumstances, an implant is employed as an adjunct to and/or for support of the remaining bone and/or bone joint. The implant is inserted adjacent to the resected bone and/or into the bone joint or void created by the osteotomy and is typically attached to the bone via bone screws or the like.

In an osteotomy such as a wedge osteotomy, a wedge-shaped portion of bone is resected, thereby leaving a wedge-shaped void. A wedge implant is then inserted to fill the wedge-shaped void. The wedge implant is a particular size in order to match the created wedge-shaped void. However, because of variants arising from the resection process, patient anatomy, or otherwise, it is desirable for the wedge implant to allow for opening or the adjustment of the created wedge-shaped void/wedge osteotomy.

Without limitation, it is therefore an object of the present invention to provide an expandable wedge implant that addresses the problems and/or inadequacies of the prior art osteotomy wedge implants and other implants for osteotomies.

SUMMARY OF THE INVENTION

An expandable wedge implant is provided for insertion into and opening of a wedge-shaped gap created by a wedge osteotomy of the extremities especially, but not necessarily, of the foot and leg.

The expandable wedge implant has first and second components that are pivotally coupled to one another, and an expansion control construct that effects implant height change by pivotal movement between the first and second constructs. The first and second components are preferably, but not necessarily, pivotally attached to one another at a rearward connection.

The expansion control construct has a threaded shaft extending between first and second ends of the first component, and a threaded ball received on the threaded shaft. The threaded ball is retained in an angled track in the second component. Rotation of the threaded shaft linearly translates the threaded ball along the threaded shaft, which also moves the threaded ball along the angled track. Movement of the threaded ball along the angled track while the threaded ball linearly translates on the threaded shaft causes the second component to pivot up and down relative to the first component, causing the wedge to expand or contract depending on direction of threaded shaft rotation.

The expandable wedge implant preferably, but not necessarily, uses three (3) anchoring members such as bone screws that are inserted through the face of the first and second components. The anchoring members protrude from the upper and lower surfaces of the implant. Different type of anchoring members may be used.

The present expandable wedge implant may be used for other types of osteotomies both of the extremities and other bones, as it is not limited to wedge osteotomies of the extremities or wedge osteotomies of other bones.

BRIEF DESCRIPTION OF THE DRAWING FIGURES

The above mentioned and other features, advantages and objects of this invention, and the manner of attaining them, will become apparent and the invention itself will be better understood by reference to the following description of the invention taken in conjunction with the accompanying drawings, wherein.

DETAILED DESCRIPTION OF THE INVENTION

Referring to FIGS. 1-9, there is shown various views of an expandable implant, generally designated 10, fashioned in accordance with the present principles, for use with a wedge osteotomy of the extremities and, particularly, for implantation into or implantation into and opening of a gap (e.g. a wedge gap) created by the wedge osteotomy. As such, the expandable implant 10 may be termed an expandable wedge implant 10 for being used in a wedge osteotomy and/or for its general shape. Herein, the term expandable wedge implant 10 will be used but is synonymous with expandable implant 10. It should therefore be appreciated that the present expandable wedge implant may be used for or with other types of osteotomies both of the extremities and other bones, as it is not limited to wedge osteotomies of the extremities or wedge osteotomies of other bones.

The expandable wedge implant 10 has a first component 12, a second component 14, and a controller 16, the nomenclature first and second being arbitrary here and throughout unless otherwise specified. The first component 12 is defined by a generally trapezoidal body 36 having a front end 37, a rear end 38, a first lateral side 39, a second lateral side 40, a top or upper surface 41, and a bottom or lower surface 42, the nomenclature front, rear, top and bottom being arbitrary here and throughout unless otherwise specified. The lower surface 42 is preferably, but not necessarily, serrated. An opening 43 is preferably, but not necessarily, provided in the body 36 extending from the upper surface 41 to the lower surface 42.

Figure 10:
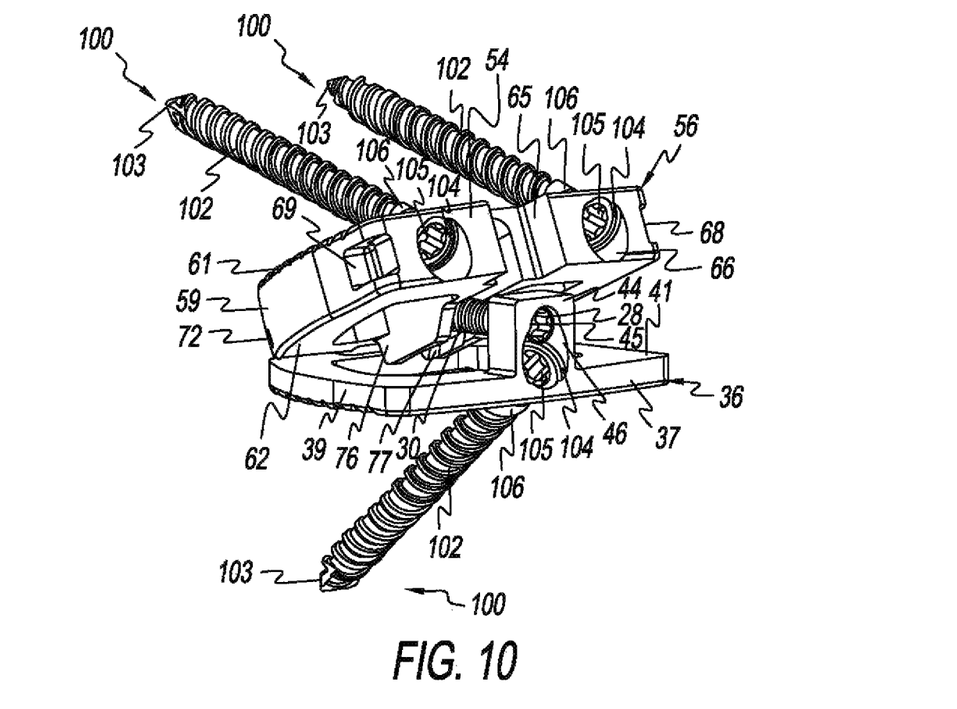
FIG. 10 is a top front isometric view of the expandable wedge implant of FIG. 1 shown in an expanded position and with anchoring screws.

The first component 12 has a boss 44 at the front end 37. A bore 45 is provided in boss 44 that extends from a front face 50 through a rear face 51 of the boss 50. The bore 45 is sized and configured to receive a head 27 on a proximal end of a cylindrical body 26 of the controller 16. A second bore 46 is also provided in the boss 44 that extends from the front face 50 to the bottom 42. The second bore 46 is sized and configured, and angled relative to the front face 50 of the boss 44, to allow an anchoring member such as a bone screw 100 to pass therethrough except for the head 104 thereof (see e.g., FIG. 10), and for the shaft 102 with tip 103 to protrude from the bottom 42 of the first component 12. Other types of anchoring members may be used.

The first component 12 has a boss 47 at the rear end 38, the boss 47 being generally medially situated. A bore 48 is provided in the boss 47 that extends from a front face 52 through a rear face 53 of the boss 47. The bore 48 is sized and configured to receive disks 32 and 33 of a distal end of the cylindrical body 26. The disks 32 and 33 are axially separated from each other to create a circumferential space 34 therebetween. The circumferential space 34 is sized to accept a portion of a tubular body 21 of a pivot pin or rod 20. The boss 47 at the rear end 38 has a bore 49 that is transverse to the bore 48 and sized to receive the tubular pivot pin body 21. The transverse bore 45 preferably, but not necessarily, intersects with the bore 48.

The head 27 of the cylindrical body 26 of the controller 16 has a socket 28 that is configured to receive and engage/disengage with a tool (not shown) for rotating the cylindrical body 26. A neck 29 axially extends from the head 27 opposite the socket 28. A threaded section or shaft 30 axially extends from the neck 29. An un-threaded cylindrical portion 31 axially extends from an end of the threaded section 30 opposite the neck 29. The disks 32 and 33 are disposed at the axial end of the un-threaded cylindrical portion 31 opposite the threaded shaft 30. The cylindrical body 26 has an axial or longitudinal length to extend from the front boss 44 to the rear boss 47.

The controller 16 also includes a ball 18 defined by a spherical body 19. A threaded bore 23 extends through the spherical body 19 and is sized to be threadedly received on the threaded shaft 30 of the cylindrical body 26. A flat is disposed on the outside of the spherical body 19. The flat is disposed generally transverse to the longitudinal axis of the threaded bore 23.

Figure 1:
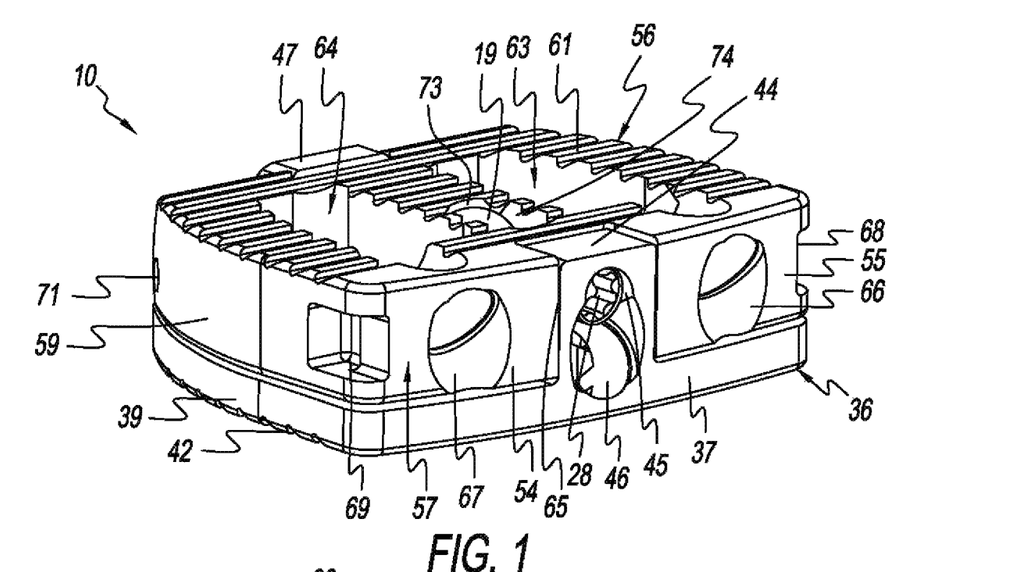
FIG. 1 is a top front isometric view of an expandable wedge implant fashioned in accordance with the principles of the present invention, the expandable wedge implant in a non-expanded position.
Figure 2:
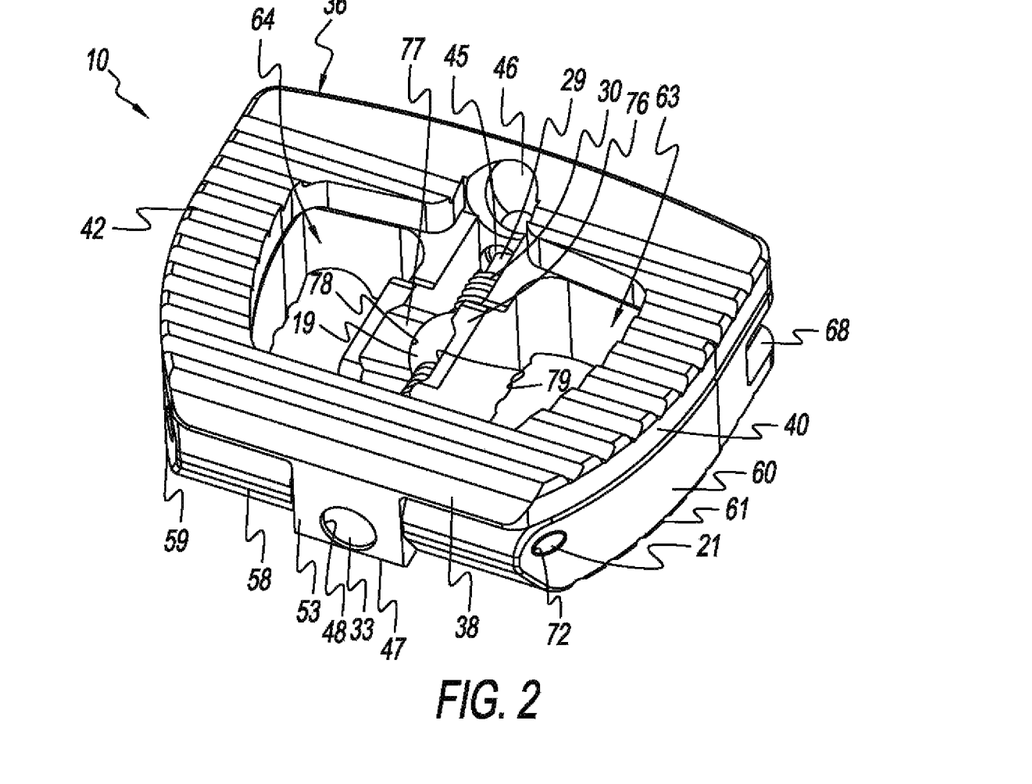
FIG. 2 is a top rear isometric view of the expandable wedge implant of FIG. 1, shown in a non-expanded position.
Figure 3:
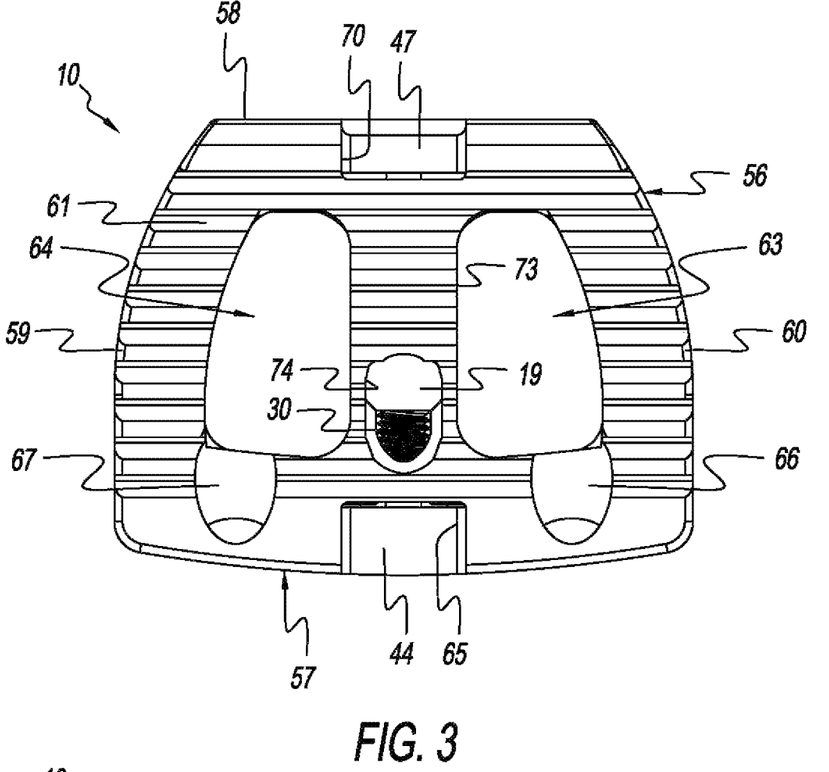
FIG. 3 is a top view of the expandable wedge implant of FIG. 1, shown in a non-expanded position.
Figure 4:
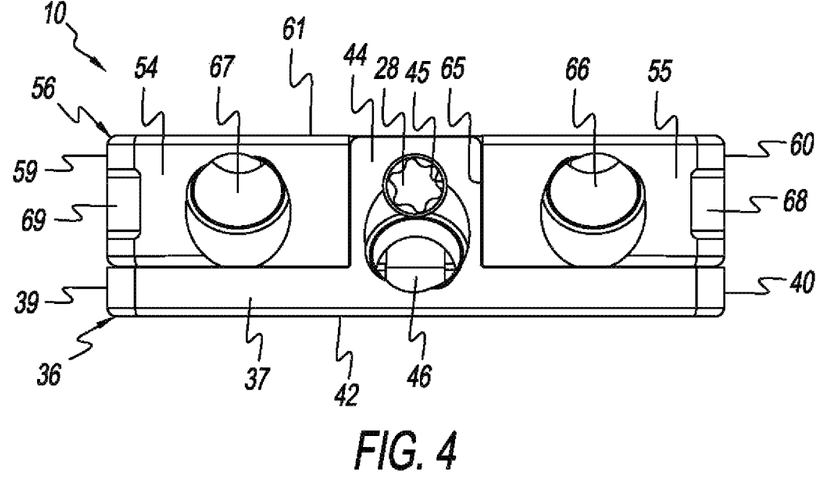
FIG. 4 is a front view of the expandable wedge implant of FIG. 1, shown in a non-expanded position.
Figure 5:
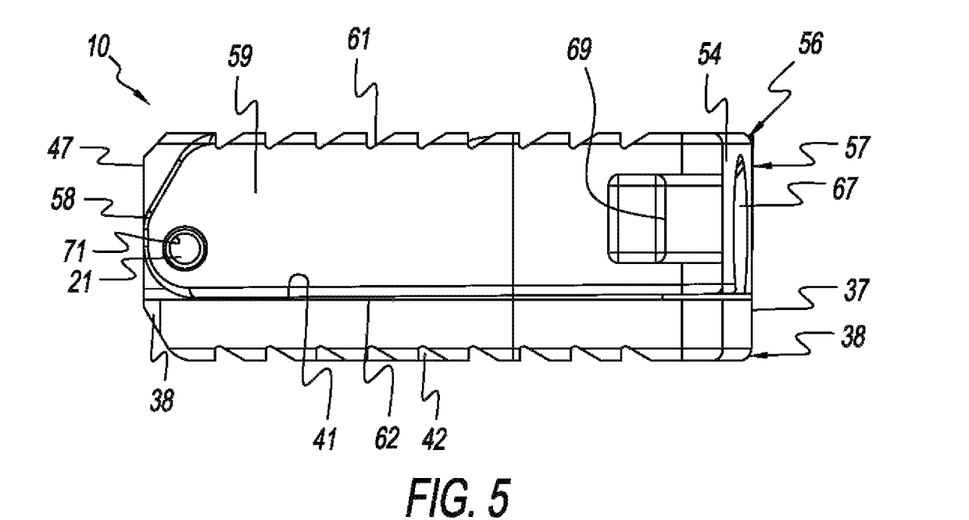
FIG. 5 is a side view of the expandable wedge implant of FIG. 1, shown in a non-expanded position.
Figure 6:
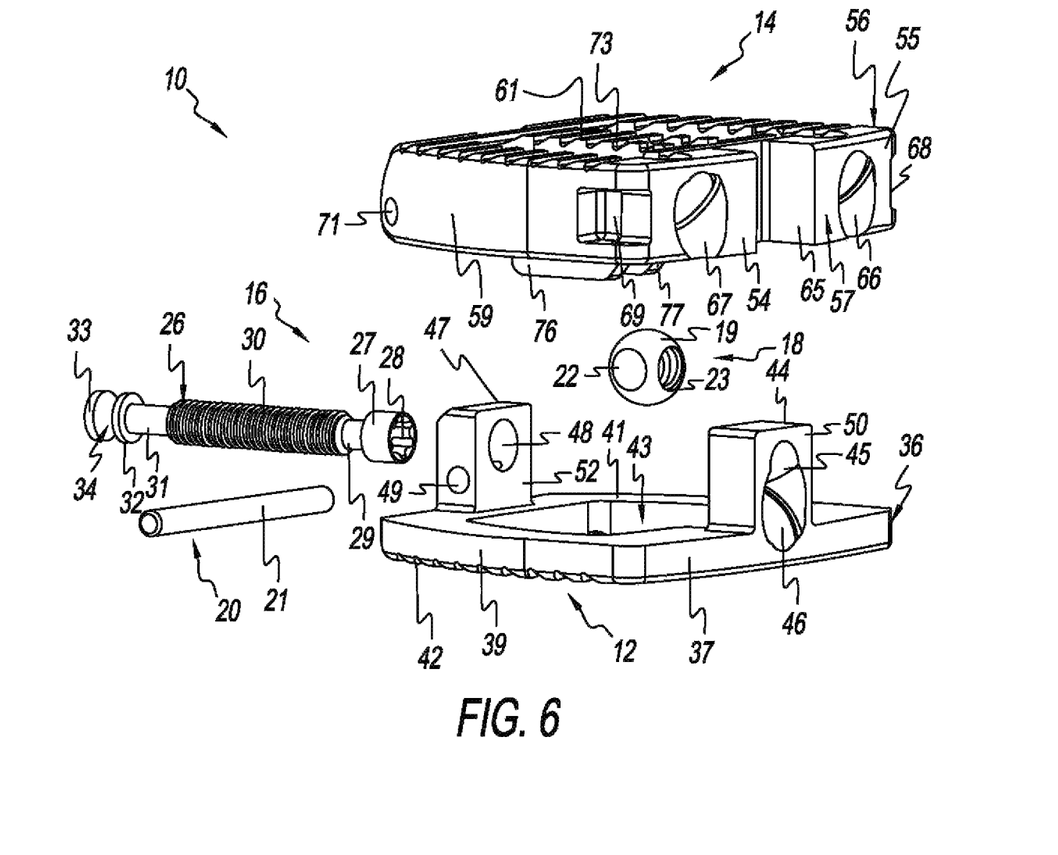
FIG. 6 is an exploded isometric view of the expandable wedge implant of FIG. 1.
Figure 7:
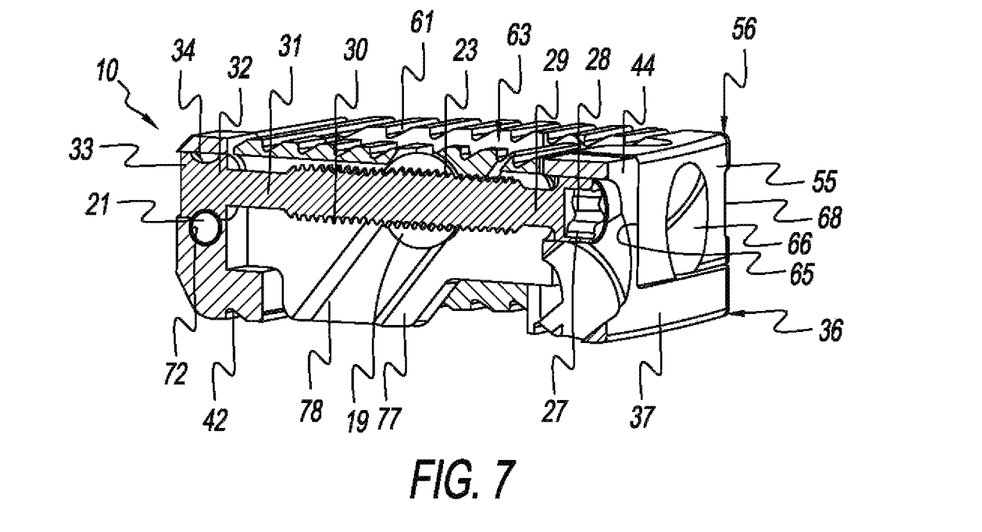
FIG. 7 is a sectional view of the expandable wedge implant of FIG. 1 in a non-expanded position.
Figure 8:
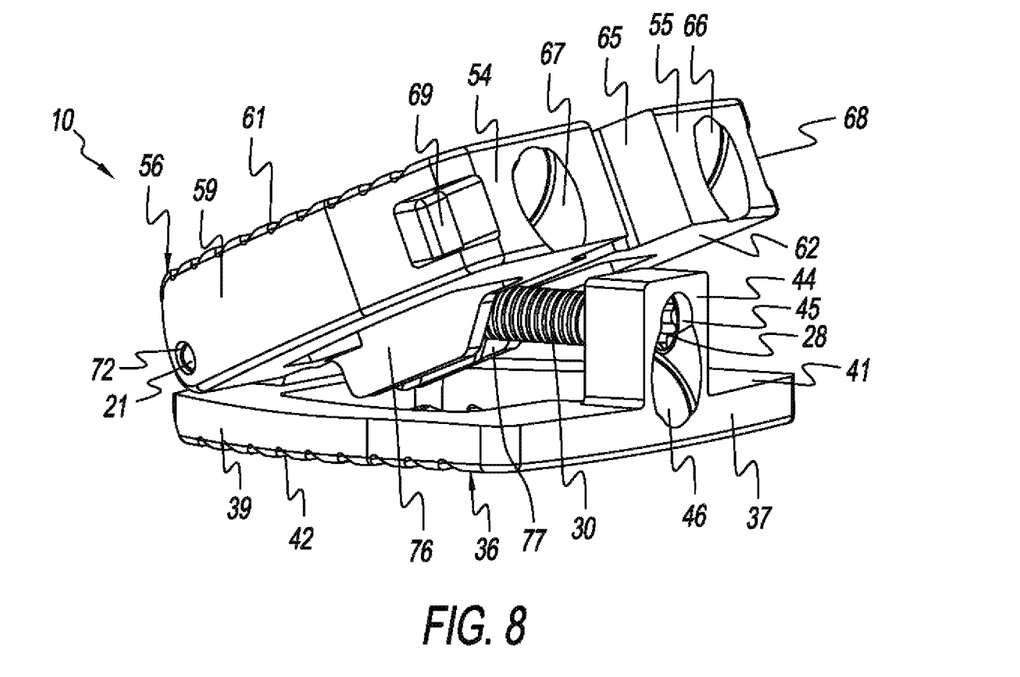
FIG. 8 is a top front isometric view of the expandable wedge implant of FIG. 1 shown in an expanded position.
Figure 9:
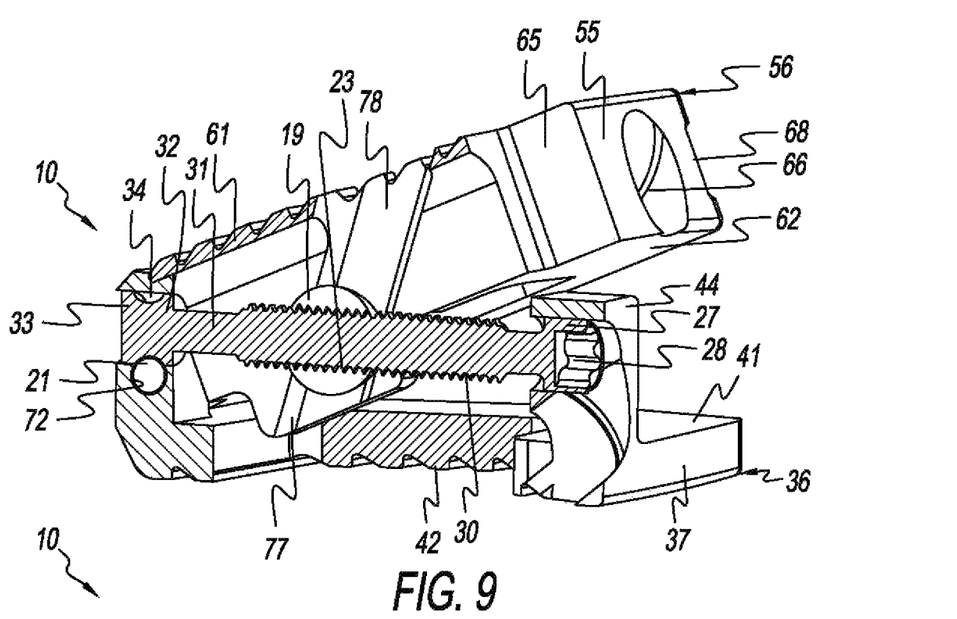
FIG. 9 is a sectional view of the expandable wedge implant of FIG. 1 shown in an expanded position.

The second component 14 is defined by a generally trapezoidal body 56 having a front end 57, a rear end 58, a first lateral side 59, a second lateral side 60, a top or upper surface 61, and a bottom or lower surface 62, the nomenclature front, rear, top and bottom being arbitrary here and throughout unless otherwise specified. The upper surface 61 is preferably, but not necessarily, serrated. A first lateral opening 64 adjacent the first lateral side 59 is preferably, but not necessarily, provided in the body 56 extending from the upper surface 61 to the lower surface 62. A second lateral opening 63 adjacent the second lateral side 60 is preferably, but not necessarily, provided in the body 56 extending from the upper surface 61 to the lower surface 62. The first and second lateral openings 64, 63 define a median 73. As best seen in FIG. 3, the median 73 has an opening 74 that allow viewing of the interior of the implant and particularly the spherical body 19 and the threaded shaft 30 of the controller 16.

The second component 14 has a first lateral boss 54 at the front end 57 and a second lateral boss 55 at the front end 57 spaced from each other to provide a central gap or notch 65. The gap 65 is sized to allow the boss 44 of the first component 12 to be received therein when the implant is closed or not pivotally expanded as when the second component 14 rests on the first component 12. A first bore 67 is provided in the first lateral boss 54 that extends from the front end 57 thereof to the top 62. The first bore 67 is sized and configured, and angled relative to the front end 57 to allow an anchoring member such as the bone screw 100 to pass therethrough except for the head 104 thereof (see e.g., FIG. 10), and for the shaft 102 with tip 103 to protrude from the top 62 of the second component 14. A second bore 66 is provided in the second lateral boss 55 that extends from the front end 57 thereof to the top 62. The second bore 66 is sized and configured, and angled relative to the front end 57 to allow an anchoring member such as the bone screw 100 to pass therethrough except for the head 104 thereof (see e.g., FIG. 10), and for the shaft 102 (connected to the underside of the head 104 via a neck 106) with tip 103 to protrude from the top 62 of the second component 14. Other types of anchoring members may be used.

The first lateral side 59 of the second component 14 includes a first notch 69 that is configured to receive an installation tool (not shown) for the implant 10. The second lateral side 60 of the second component 14 includes a second notch 68 that is configured to receive the installation tool (not shown). The rear end 58 of the body 56 has a medial notch 70 that is sized to receive the boss 47 of the first component 12. A first lateral pivot pin bore 71 is provided at the first lateral rear end of the body 56 and a second lateral pivot pin bore 72 is provided at the second lateral rear end of the body 56, each one sized to receive the cylindrical pivot pin body 21. The pivot pin 21 extends through the first and second lateral pivot pin bores 71, 72 and the pivot pin bore 49 of the rear boss 47 of the first component 12 to pivotally couple the first and second components 12, 14 together (akin to a clamshell). Pivoting of the first and second components 12, 14 relative to one another create a change in implant height. Pivoting is controlled by the controller 16.

The second component 14 has a first flange 76 that extends from the lower surface 62 on one side of the window 74 and a second flange 77 that likewise extends from the lower surface 62 on the other side of the window 74 such that the first and second flanges 76, 77 are spaced from one another. The first and second flanges 76, 77 are generally medially situated on the lower surface 62. The first flange 76 has a first groove or channel 79 that extends from a lower edge thereof to the lower surface 62 and is angled from the rear to the front of the component 14. The channel 79 is generally flat and thus receives the flat 22 of the ball 19. The second flange 77 has a second groove or channel 78 that extends from a lower edge thereof to the lower surface 62 and is angled from the rear to the front of the component 14. The channel 78 is generally curved in like shape to the spherical ball 19. The first and second channels 79, 78 form an angled track for the spherical ball 19.

As can be discerned from the figures, the controller 16 operates as follows. Rotation of the screw 16 causes the ball 19 to linearly (axially) travel, translate or move along the threaded shaft 30 of the screw 16. Direction of rotation of the screw 16 determines axial direction of ball 19 movement. When the direction of screw 16 rotation causes the ball 19 to travel rearward, the ball 19 travels within the angled track towards the bottom of the angled track and the bottom 62 of the second component 14 and towards the first component 12, pivoting the second component 14 away from the first component 12 to open or expand the implant to increase implant height. The amount of ball travel determines the amount of pivoting or height increase. When the direction of screw 16 rotation causes the ball 19 to travel forward, the ball 19 travels within the angled track towards the top of the angled track away from the first component 12 and to the second component 14, pivoting the second component 14 toward the first component 12 to close or contract the implant to decrease implant height.

Figure 11:
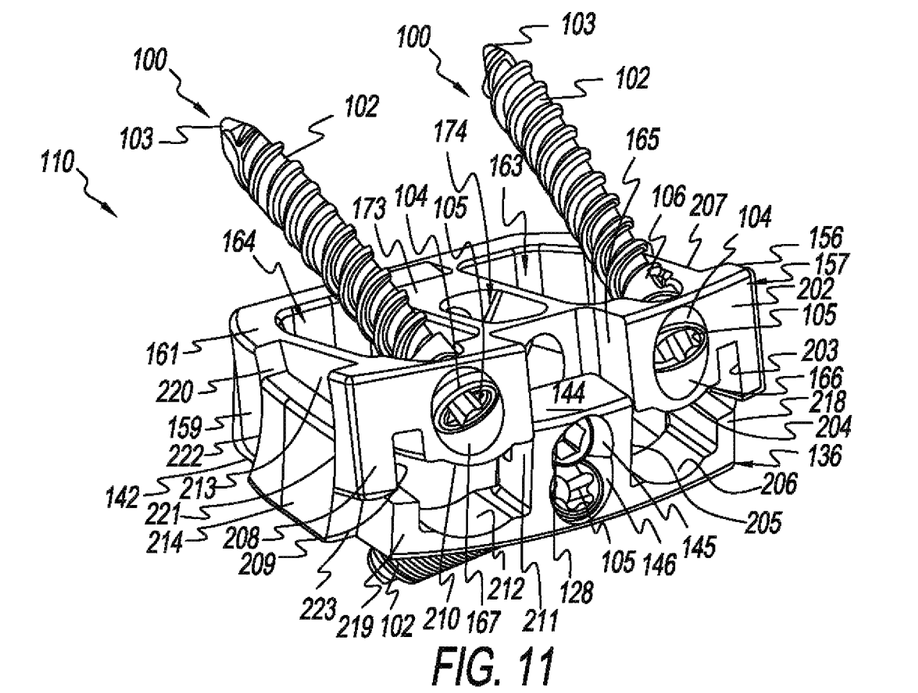
FIG. 11 is a top front isometric view of an expandable wedge implant fashioned in accordance with the principles of the present invention, the expandable wedge implant shown in a non-expanded position and with anchoring screws.
Figure 12:
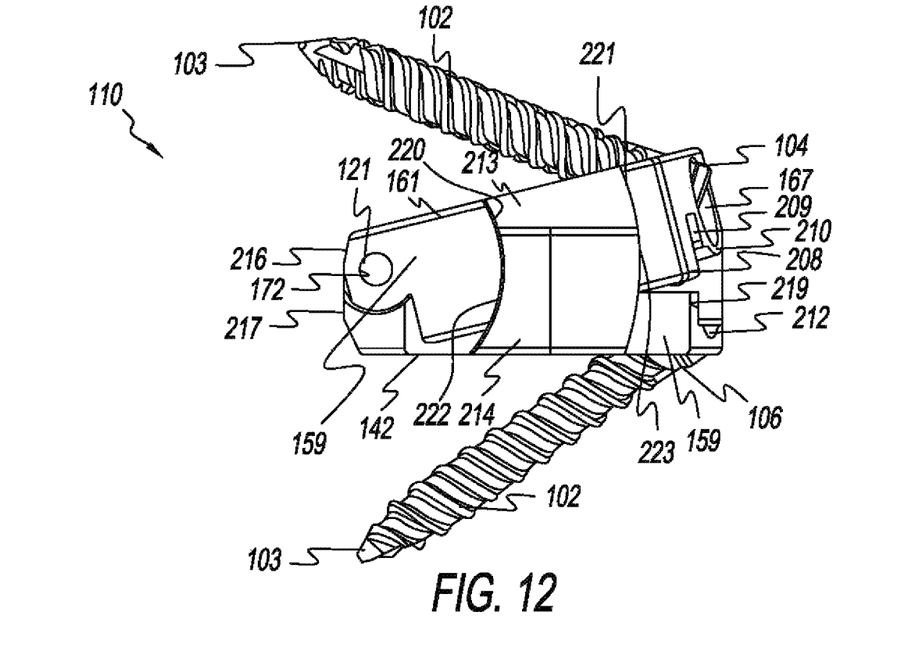
FIG. 12 is a side view of the expandable wedge implant of FIG. 11 shown in an expanded position and with anchoring screws.
Figure 13:
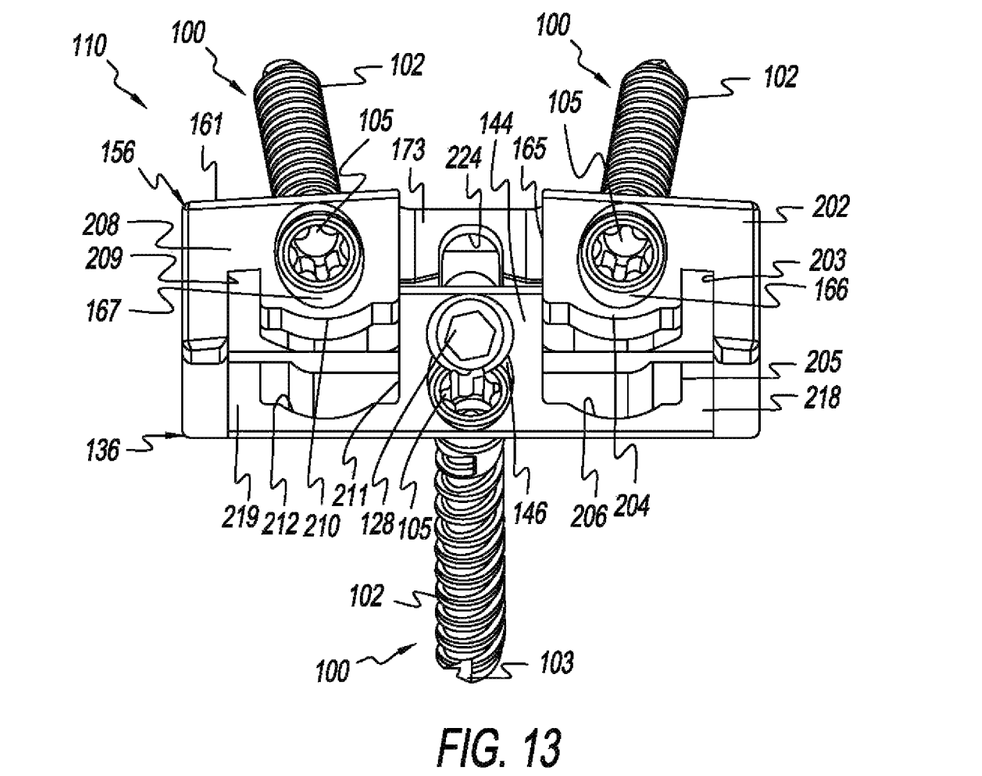
FIG. 13 is a front view of the expandable wedge implant of FIG. 11 shown in an expanded position and with anchoring screws.

FIGS. 11-13 show an expandable wedge implant 110 having a variation of the expandable wedge implant 10. As such components, features, functions and the like that are the same have the same callout number as the implant 10 except labeled in the 100s (e.g. first component body 136 of implant 110 corresponds first component body 36 of implant 10). Some components of implant 110 are not labeled as the component, feature or function is evident as being the same as those of the implant 10.

The implant 110 differs in the size of the second component 114 relative to the first component 112—the second component 113 oversized relative to the first component 112, as well as the interface between the first and second components 112, 114. The front boss 144 has a first flat lateral side 205 that faces a first lateral side member 202 having a first vertical slot 203 distal the first flat lateral side 205 and a first convex bottom 204. The first vertical slot 203 receives a first lateral vertical portion 218 of the first component 112 when the second component 114 is closed, non-pivoted, or not expanded relative to the first component 112. The first component 112 has a first lateral curved surface 206 adjacent the first flat lateral side 205 that receives the first convex bottom 204 of the first lateral side member 202 when the second component 114 is closed, non-pivoted, or not expanded relative to the first component 112.

The front boss 144 has a second flat lateral side 211 that faces a second lateral side member 208 having a second vertical slot 209 distal the second flat lateral side 211 and a second convex bottom 210. The second vertical slot 209 receives a second lateral vertical portion 219 of the first component 112 when the second component 114 is closed, non-pivoted, or not expanded relative to the first component 112. The first component 112 has a second lateral curved surface 212 adjacent the second flat lateral side 211 that receives the second convex bottom 210 of the second lateral side member 208 when the second component 114 is closed, non-pivoted, or not expanded relative to the first component 112.

As best seen in FIG. 12, the rear 217 of the first component 114 interfaces with the rear 216 of the second component 114. A first lateral side of the first component 112 has an outward projecting boss 214 having a rear curved (concave) surface 222 and a front curved (convex) surface 221. A first lateral side of the second component 114 has an inward notch 213 having a rear curved (convex) surface 220 and a front curved (concave) surface 221. The boss 214 thus moves within the notch 213. The controller 116 has the same components, features and functions and thus operates in the same manner as the controller 16.

The second lateral side of the implant 110 not seen has the same components, features and functions as the first lateral side of the implant 110 shown in FIG. 12 and discussed above. As such, they will not be discussed with reference to the second lateral side.

Figure 14:
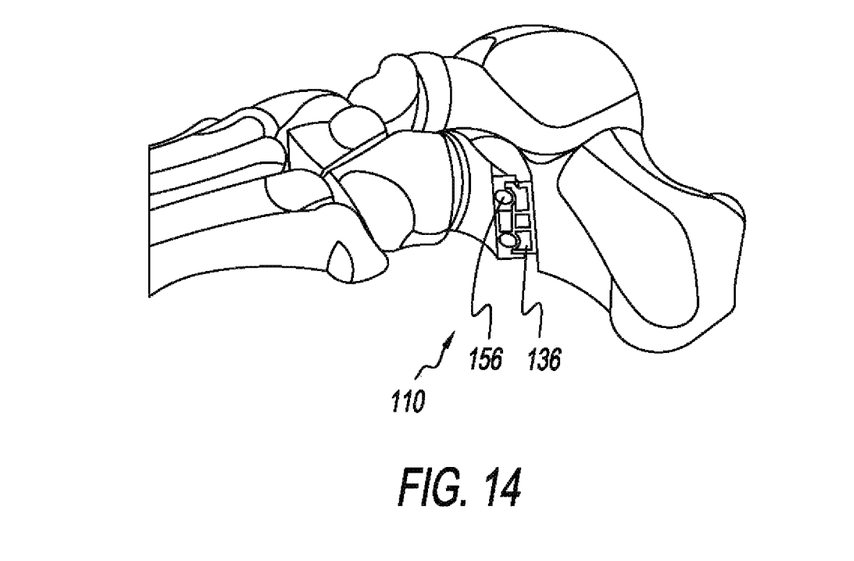
FIG. 14 is an isometric view of an ankle having undergone an osteotomy with the expandable wedge of FIGS. 11-13 implanted therein and in an expanded position.

FIG. 14 shows an ankle having undergone an osteotomy with the expandable wedge implant 110 installed in the wedge-shaped osteotomy gap formed by the osteotomy. The expandable wedge implant 110 has been expanded, with the components 136 and 156 therefore pivoted relative to one another to fill the wedge-shaped osteotomy gap.

It should be appreciated that the present expandable wedge implant may be used for orthopedic purposes other than osteotomies of the extremities. Additionally, the dimensions of the various components, features, and mechanisms of the present expandable wedge implant may be modified as desired within the spirit and scope of the present invention.

What is claimed is:

1. An expandable implant for wedge osteotomies of the extremities comprising:
  a pivot pin;
  a first component having a first component front end, a first component rear end, and a first component pivot structure having a first component boss at the first component rear end with a first component pivot bore extending through the first component boss;
  a second component having a second component front end, a second component rear end, and a second component pivot structure, the second component pivot structure connected to the first component pivot structure to pivotally couple the second component to the first component and having a second component first boss at a first lateral side of the second component rear end with a second component first pivot bore extending through the second component first boss, and a second component second boss at a second lateral side of the second component rear end with a second component second pivot bore extending through the second component second boss;
  the first component boss laterally disposed between the second component first boss and the second component second boss;
  the pivot pin extending through the second component first pivot bore, the first component pivot bore, and the second component second pivot bore to pivotally join the first and second components; and
  a controller operably connected to the first component and to the second component, the controller effecting implant expansion through pivotal movement of the first and second components, the controller comprising:

a threaded shaft having a proximal end and a distal end, the distal end of the threaded shaft retained at the first component rear end and the proximal end of the threaded shaft retained at the first component front end such that the threaded shaft extends from the first component rear end to the first component front end;

a ball having a threaded bore extending through the ball, the ball threadedly disposed on the threaded shaft for linear movement on and along the threaded shaft; and an angled track formed in the second component adjacent the threaded shaft, the ball movably retained in the angled track;

whereby rotation of the threaded shaft in one rotational direction causes the ball to linearly translate along the threaded shaft in one linear direction and to move within the angled track in one angular direction to cause the second component to pivot relative to the first component to effect an increase in implant height.

2. The expandable implant of claim 1, wherein:

the first component boss includes a first shaft bore extending through the first component boss transverse to the first component pivot bore that is configured to rotatably receive the distal end of the threaded shaft; and the first component front end has a first component second boss with a second shaft bore extending through the first component second boss coaxial with the first shaft bore of the first component boss that is configured to rotatably receive the proximal end of the threaded shaft.

3. The expandable implant of claim 2, wherein:

the proximal end of the threaded shaft has a proximal head with a socket configured to receive a tool to rotate the threaded shaft;

the first shaft bore of the first component boss intersects the first component pivot bore;

the distal end of the threaded shaft has a circumferential groove that is adjacent the first component pivot bore; and the pivot pin extends along the circumferential groove.

4. An expandable implant for wedge osteotomies of the extremities comprising:

a first component having a first component front end, a first component rear end, a first component pivot structure, and a first surface transverse to the first component front end and the first component rear end;

a second component having a second component front end, a second component rear end, and a second component pivot structure, the second component pivot structure connected to the first component pivot structure to pivotally couple the second component to the first component, and a second surface transverse to the second component front end and the second component rear end, and adjacent to the first surface of the first component;

the second component further has a first flange on the second surface that extends transverse to the second surface, and a second flange on the second surface that extends transverse to the second surface and adjacent to the first flange, the first flange having a first angled channel and the second flange having a second angled channel opposite the first angled channel, the first angled channel and the second angled channel forming an angled track of the second component; and a controller operably connected to the first component and to the second component, the controller effecting implant expansion through pivotal movement of the first and second components, the controller comprising:

a threaded shaft having a proximal end and a distal end, the distal end of the threaded shaft retained at the first component rear end and the proximal end of the threaded shaft retained at the first component front end such that the threaded shaft extends from the first component rear end to the first component front end;

a ball having a threaded bore extending through the ball, the ball threadedly disposed on the threaded shaft for linear movement on and along the threaded shaft; and the angled track formed in the second component adjacent the threaded shaft, the ball movably retained in the angled track;

whereby rotation of the threaded shaft in one rotational direction causes the ball to linearly translate along the threaded shaft in one linear direction and to move within the angled track in one angular direction to cause the second component to pivot relative to the first component to effect an increase in implant height.

5. The expandable implant of claim 4, wherein:

the ball has a flat formed on its outer surface transverse to the threaded bore, the flat received in the second angled channel of the second flange.

6. The expandable implant of claim 5, wherein:

the first angled channel of the first flange has an arced surface configured to receive the ball opposite the flat.

7. The expandable implant of claim 5, wherein:

a first component boss has a first anchoring member bore configured to receive and retain a first anchoring member and to make a threaded portion of the first anchoring member angularly extend from the first component; and the second component front end has a first lateral side, a second lateral side, a second anchoring member bore at the first lateral side and configured to receive and retain a second anchoring member and to make a threaded portion of the second anchoring member angularly extend from the second component, and a third anchoring member bore at the second lateral side and configured to receive and retain a third anchoring member and to make a threaded portion of the third anchoring member angularly extend from the second component.

\* \* \* \* \*